United States Patent [19]

Scherrer et al.

[11] Patent Number: 5,059,521

[45] Date of Patent: Oct. 22, 1991

[54] MONOCLONAL ANTIBODIES AGAINST PROSUMAL PROTEINS

[75] Inventors: Klaus Scherrer, Paris; Maria-Fatima Grossi de Sa, Gentilly, both of France

[73] Assignee: Pro-Soma, Paris, France

[21] Appl. No.: 298,791

[22] Filed: Jan. 17, 1989

Related U.S. Application Data

[63] Continuation of Ser. No. 902,226, Aug. 29, 1986, abandoned.

[30] Foreign Application Priority Data

Aug. 30, 1985 [FR] France ................. 85 12946

[51] Int. Cl.$^5$ ................ G01N 33/53; G01N 33/577; G12N 15/00; C07K 15/14
[52] U.S. Cl. ................ 435/7.1; 435/7.23; 435/172.2; 435/240.27; 435/810; 435/960; 436/501; 436/503; 436/536; 436/548; 436/64; 436/808; 436/813; 530/387; 530/808; 935/95; 935/103; 935/106; 935/110
[58] Field of Search ............. 436/548, 536, 506, 507, 436/508, 813, 501, 503, 63, 64, 808; 435/6, 7, 172.2, 240.27, 7.1, 7.21, 7.23, 7.24, 7.25, 960, 810, 188; 530/387, 808, 350; 424/85.8; 935/95, 103, 106, 110

[56] References Cited

U.S. PATENT DOCUMENTS 4,444,744  7/1984  Goldenberg .................. 424/1.1
4,448,890  5/1984  Smetana et al. ............... 436/508

OTHER PUBLICATIONS

Chemical Abstract, Pisetsky et al., vol. 101, Abst. No. 53111x, 1984.
Schmid et al., The EMBO Journal, vol. 3, No. 1, 1984, pp. 29–34.
Whittingham, Journal of Immunological Methods, vol. 61, 1983, pp. 73–81.
Billings et al., J. of Immunology, vol. 135, No. 1, Jul. 1985, pp. 428–432.
Choi et al., Proc. Natl. Acad. Sci., U.S.A., vol. 81, Dec. 1984, pp. 7471–7475.
Sevier et al., Clin. Chem., vol. 27(11), 1981, pp. 1797–1806.
Schuldt et al., "Analysis of Cytoplasmic 19 S Ring-Type Particles in Drosophilia which Contain hsp 23 at Normal Growth Temperature," *Dev. Biol.*, 110(1), 65–74 (Jul. 1985).
Martins de Sa et al., "Prosomes and the Heat-Shock Complex," *Molecular and Cellular Biology*, vol. 9, pp. 2672–2661 (1989).
Naraya et al., "Minute Ring-Shaped Particles in Cultured Cells of Malignant Origin", *Nature New Biology*, (243) 146–150 (1973).
Domae et al., "Donut Shaped 'Miniparticles' in Nuclei of Human and Rat Cells," *Life Sciences*, (30), 469–477 (1982).
Arrigo et al., "Characterization of the Prosome from Drosophilia and its Similarity to the Cytoplasmic Structures Formed by the Low Molecular Weight Heat-Shock Proteins," *The EMBO Journal*, 4(2) 399–406 (Feb. 1985).

*Primary Examiner*—Esther L. Kepplinger
*Assistant Examiner*—Florina B. Hoffer
*Attorney, Agent, or Firm*—Donna Bobrowicz; William M. Blackstone

[57] ABSTRACT

The invention relates to monoclonal antibodies against prosomal proteins of a prosome, said prosome having a sedimentation coefficient of approximately 19S, and to a method for detecting cancer using monoclonal antibodies specifically directed against said prosomal proteins. The invention also relates to diagnostic reagents for use in such a detection method.

17 Claims, 4 Drawing Sheets

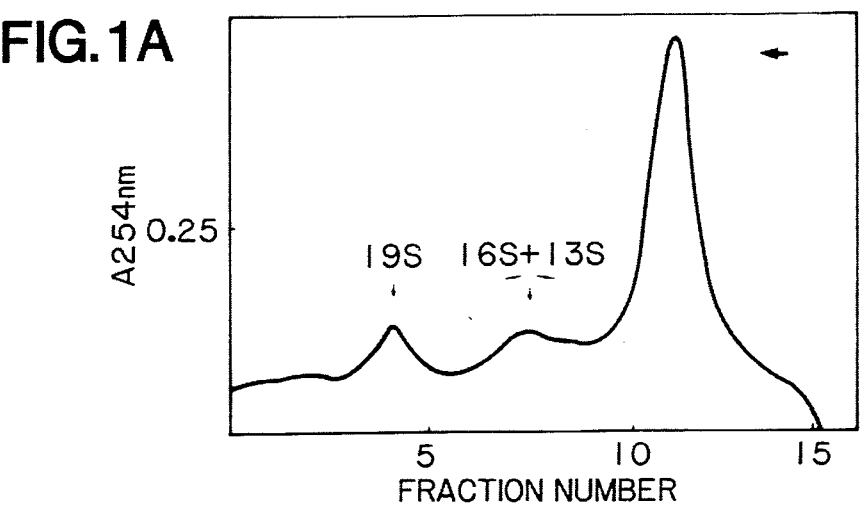
FIG.1A
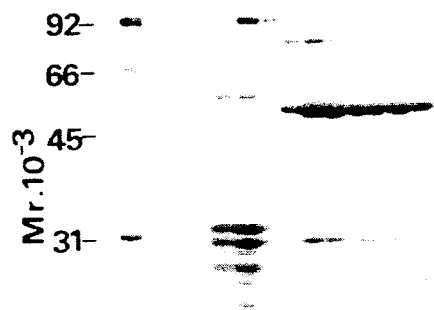
FIG.1B
FIG.1C-1
FIG.1C-2

MONOCLONAL ANTIBODIES AGAINST PROSUMAL PROTEINS

This is a file wrapper continuation of application Ser. No. 06/902,226 filed Aug. 29, 1986 now abandoned.

The present invention relates to monoclonal antibodies against prosomal proteins, to cell lines producing these antibodies, to a method for immuno-chemical diagnosis, and to a diagnostic reagent for use with this method.

Prosomes are ribonucleoprotein (RNP) complexes or RNP particles which have recently been demonstrated by biochemical methods and have been visualized by electron microscopy, in particular in the cytoplasm of duck and mouse erythroblasts and in human HeLa cells [defined by SPOHR et al., Eur. J. Biochem. 17, 296–318, (1970)]. To this end, reference may be made to the paper by Schmid et al. in the EMBO Journal 3(1), 29–34, (1984), cited in the present description by way of reference.

The molecular weight of prosomes has been estimated at approximately 600,000 daltons. Prosomes are extremely stable complexes. Indeed, they are resistant to ribonuclease, to protease K, to solutions of caesium ions greater than 1M and, in the cells mentioned above, to 1% strength solutions of the detergent "Sarkosyl" (sodium N-lauroylsarcosinate) which can be shown to dissolve the other constituents of repressed mRNPs.

These complexes, which have a sedimentation coefficient of approximately 19S, contain, according to the cell type and species, 1 to 12 small RNAs and one or more members of a characteristic population of proteins which contains both species-specific members and members common to all species. The molecular weight of these member proteins varies between 19,000 and 50,000, and the number of molecules of proteins per prosome is of the order of 20.

The population of prosomal proteins comprises at least 25 distinct members; in consequence, a minimum of approximately 25 different types of prosomes can exist.

Up to the present time the physiological and diagnostics significance of the prosomes has remained unclear. However, now we have indications that prosomes may be involved in many vital physiological processes related to the differentiation of cells and even of whole organisms, to the communication between cells, and to autoimmune disease.

For example, we have found now a differential distribution of prosomes, indicating a physiological specificity which correlates with the functional state of the cell and of the organism during embryonic development and cellular differentiation.

More specifically, in the epithelium of embryos, a certain type of prosomal antigen could be demonstrated in the nucleus, then subsequently in the cytoplasm and then in sectors of the cytoplasm, according to the different stages of differentation.

Another remarkable finding is that in certain instances prosomes are present which very probably are composed exclusively of multiple copies of a single protein component linked to the prosomal RNA. We have also found that not only the quantitative distribution of the prosomes varies with the stage of erythroblast differentiation but that furthermore the various prosomal proteins differ in their distribution through the subsequent differentiation stages, although the proteins in the nucleus are found to have the same molecular weight as those in the cytoplasm.

It can be shown that prosomes are forming part of a network that spans the cell from the chromosome to the plasma membrane and beyond. This suggests a correlation between the cells dynamic architecture and consecutive steps of the cascade of gene expression and control—the main role attributed to the prosomes. Determination and in particular differential detection of prosomes and prosomal proteins then should be considered as a powerful tool for diagnosing disorders associated with disturbance of gene control—as is, for example, the case with cancer.

Prosomes hence represent a new class of cell components which, by their structure and presence, reflect the physiological state of a given cell.

It has hence proved necessary to have means at one's disposal for identifying prosomes, for example in order to:

A) for experimental purposes:
   1) analyse the detailed structure of living human or animal cells;
   2) study the control of gene expression after transcription; and B) for diagnostic purposes:
   1) define a disturbance of the prosomal immune phenotype of a given cell in relation to a pathological state or a pathogen;
   2) identify cells in relation to their state of differentiation and development, for example identify the cells of embryonic type among adult cells.

Therefore the present invention is concerned with monoclonal antibodies directed against prosomal proteins, which are useful, for example, in the detection of prosome-related phenomena, and can be applied also therapeutically in certain prosome-related disorders.

Therefore, the present invention is also concerned with a method for detecting prosome-related phenomena, and in particular for diagnosing prosome-related disorders in a sample comprising incubating said sample with monoclonal antibodies specifically directed against at least one prosomal protein, wherein the monoclonal antibodies are directly or indirectly provided with a label, and subsequently determining the binding of said label to the prosomal protein and/or to said monoclonal antibodies.

In the method according to the invention the sample either can be tissue material (preferably a section thereof suited for microscopic examination) or a liquid medium (such as blood or a fraction thereof, urine or lymphoid fluid) derived from the living being to be diagnosed, or in some instances the complete living being itself (e.g. in imaging).

Therefore the present invention is also concerned with the diagnostic reagent comprising a monoclonal antibody specifically directed against a prosomal protein, coupled to a label.

The label for use with the method according to the invention may be any label generally used in immunoassays. Examples thereof are radio-active atoms or compounds, enzymes, particles such as erythrocytes, latex particles, dispersed sol particles of dyes, metals or metal compounds, chromophores, fluorophores, etc. The label can be bonded directly or indirectly to the monoclonal antibodies. A direct bond can be established preferably by a covalent linkage, optionally using a linker molecule. An indirect linkage between label and monoclonal antibody can be established for example by reacting the monoclonal antibody with a labelled specific antigen, or with second antibody or fragment thereof or with protein A or a similar compound, or for example by using a monoclonal antibody to which avidine or biotin is bound and reacting this with labelled biotin or avidine, respectively.

According to the invented method applied to a liquid sample, any type of usual immuno-assay can be applied. To name a few: sandwich-assay, solid-phase-competition-assay, agglutination-assay or agglutination-inhibition-assay. In a sandwich-assay, generally the antigen to be detected is sandwiched between an antibody immobilized or to be immobilized to a solid surface on the one hand and an antibody which is labelled or to be labelled on the other hand. In a solid-phase-competition the antigen to be determined for example can be incubated with a solid-phase-bound antibody and a labelled antigen. In an agglutination-assay the antigen to be determined is incubated with particle-bound antibodies, which will aggregate and form a precipitate upon antigen binding. On the other hand in an agglutination-inhibition-assay, particle-bound antigens as well as free antibodies may be incubated with the antigen to be determined.

In cases wherein tissue material is used as a sample with the method according to the invention, this tissue material optionally first can be fixed and subsequently can be incubated with the monoclonal antibodies which are labelled or to be labelled, optionally after first fixing the material by chemical or physical means.

The labels used according to the invention are observed for their binding after incubation either visually or by instrumental methods depending on the type of label and type of assay used.

The monoclonal antibodies specifically directed against prosomal proteins are produced by biologically pure cell lines of immortalized antibody-producing cells.

Such immortalized antibody-producing cells can be obtained according to any of the various methods which are known in the art, and which generally go through the steps of 1. inducing suitable cells such as lymphocytes to production of specific antibodies; 2. immortalizing said cells; and 3. selecting clones out of these immortalized cells which produce antibodies of the desired specificity and affinity. An often used method was first described in 1975 by Köhler and Millstein [Nature 256, 495–497 (1975)] and comprises immunizing mice with the antigen against which antibodies are wanted, isolating spleen cells and fusing these with mouse myeloma cells to obtain so-called hybridomas. However, animals other than mice can be immunized as well, and antibody-producing cells from other parts of the body will be suitable as well. Furthermore, these antibody-producing cells alternatively can be immortalized by other methods such as transformation of the cells with immortalizing transforming genetic material, such as Eptein-Barrvirus or oncogenic DNA.

As stated above, according to the present invention the monoclonal antibodies against prosomal proteins are suitable for the detection or identification of prosomes by classical techniques of immunological determination, such as immunofluorescence and immunoenzymatic or radioimmunological techniques.

The application of the method according to the invention has considerable importance, both in the field of experimental research in biology and in the field of medical research, in particular cancer research, and in clinical medicine for the diagnosis of diseases by differential immune phenotyping.

For example, in the field of experimental research in biology, the method according to the invention can be used for the characterization of structure, function and synthesis of prosomes in the role of ubiquitous physiological complexes. In particular, the differential cytological localization of individual types of prosomes, according to the methods of cell fractionation and of biochemistry, or by immunofluorescence on intact cells or tissue sections, can be greatly facilitated by means of the method according to the invention.

In developmental biology, given the presence or absence of prosomes and the characteristic cytological localization of specific prosomes in cells of a specific type, the prosomal monoclonal antibodies are useful for the characterization, identification and tracking of specific cells in the embryonic development, thereby enabling, as it were, a dynamic microanatomy to be established in terms of the development. Inasmuch as prosomes are involved in the differential control of gene expression, the method according to the invention can be used for analyzing the mechanisms underlying cell regulation.

In the field of medical research, the method according to the invention will, by means of differential immune phenotyping, enable a veritable atlas of distribution of prosomal antigens to be established according to the type of cells of specific tissues and the stage of differentiation of the cells. The modification of this distribution in the case of pathological conditions affecting the regulation, and hence the physiological state, of the cells will be able to be identified using the method according to the invention.

For the clinical diagnosis of pathological conditions of diverse origins, the method according to the invention will offer an essential tool. In effect, this method will enable the presence and distribution of cells which deviate from the normal to be recognized rapidly in sections of tissues removed, for example, by biopsy, and in physiological fluids. In this manner, the diagnosis of pathological conditions which currently require a high degree of expertise in cytology and microanatomy may be automated by means of differential cytofluorimetry.

As regards cancer, the method according to the invention may be very useful for detecting the presence of cells in peripheral blood at an early stage of development. In effect, normal peripheral blood contains only a very small number of immature cells. In contrast, in the peripheral blood of a leukaemia patient, the presence of a considerable number of immature cells is noted.

BRIEF DESCRIPTION OF THE DRAWINGS

FIG. 1A shows the sedimentation profile of the duck 20S globin mRNP particle in a sucrose gradient. FIG. 1B is a photograph of the one-dimensional SDS-polyacrylamide gel of the proteins in the fraction of the gradient shown in FIG. 1A. FIGS. 1C-1 and 1C-2 are photographs of the proteins in a gel homologous with the gel shown in FIG. 1B after transfer to nitrocellulose and successive reaction with monoclonal antibodies against protein p27K and protein p31K respectively.

FIG. 3A-1 is a photograph of duck peripheral blood cells which have reacted with the antibody against protein p27K; FIG. 3A-2 is a photograph of duck peripheral blood cells which have reacted with the antibody against protein p31K.

FIG. 4A-1 shows Hela cells incubated with the monoclonal antibody against protein p27K; FIG. 4B-2 shows Hela cells incubated with the monoclonal antibody against protein p31K.

Figures 2A, 2B, 2C:
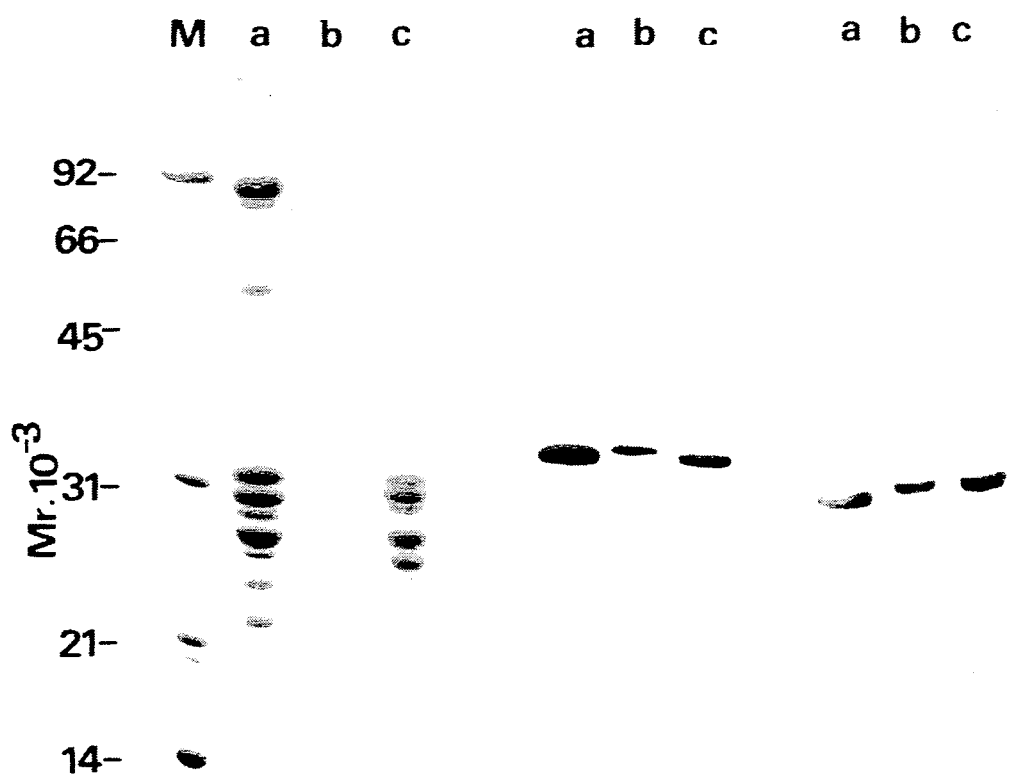
FIG. 2A is a photograph of the gel from electrophoresis of the proteins of duck erythrocytes (a), mouse erythrocytes (b) and Hela cells (c).
FIGS. 2B and 2C are photographs of the proteins in a homologous gel after transfer to nitrocellulose paper and reaction with the monoclonal antibodies against protein p31K and protein p27K respectively.

The present invention will now be described in greater detail by means of the illustrative examples below.

EXAMPLE 1

Isolation of prosomal proteins

The proteins are extracted from the prosomes by gel electrophoresis, the prosomes having been separated beforehand from the other cellular complexes by fractionation on a sucrose gradient.

The production of the prosomal proteins hence consists in:

1) the separation of the prosomes from the other cellular complexes by fractionation by differential centrifugation and on a sucrose gradient, and recovery of the particles which have a sedimentation coefficient of approximately 19S;
2) extraction of the sought protein by gel electrophoresis.

The production of duck and mouse prosomes has been described in detail by SCHMID et al. in the EMBO Journal 3(1), 29–34, (1984).

HeLa cell prosomes were obtained according to the procedure described below:

1) post-mitochondrial supernatants were prepared from cultures of Hela cells according to the method described by GANDER et al. (Eur. J. Biochem. 38, 443–452, 1973);
2) preparations of polyribosomes and post-ribosomal particles were then prepared according to the method described by VINCENT et al. (Eur. J. Biochem., 112, 617–633, 1980);
3) the free cytoplasmic ribonucleoprotein complexes were fractionated by sedimentation of pellets of post-ribosomal particles resuspended in 15 to 28% strength (weight/weight) isokinetic sucrose gradients in buffer having a low salt content, the composition of which is as follows: 10 mM thriethanolamine. HCl (pH 7.4), 50 mM KCl and 5 mM 2-mercaptoethanol. Such a fractionation was carried out in a "Beckman" zonal rotor of type Ti 14, for 15 h. at 41,000 rpm and at 4° C.;
4) the particles which sedimented within the range 15 to 30S were then recombined and concentrated by high speed centrifugation in a "Beckman" type Ti 60 rotor for 18 h. at 48,000 rpm and at 4° C.;
5) the centrifugation pellet was placed on a sucrose gradient (5 to 21% weight/weight) in the presence of KCl at a concentration of 0.5M (Rotor SW 41 37,000 rpm, 17 h., 4° C.) and the fraction which sedimented at approximately 19S was collected.

In all cases, the prosomal proteins are extracted from these fractions and identified using known techniques of gel electrophoresis, for example, electrophoresis on one-dimensional sodium dodecyl sulphate (SDS)-polyacrylamide gels according to LAEMMLI (Nature 227, 680–685, 1970) or electrophoresis on two-dimensional gels as described by O'FARRELL et al. (Cell 12, 1133–1142, 1977). The molecular weight markers used in these electrophoretic procedures were the following compounds: phosphorylase-b(94K), bovine serum albumin (68K), ovalbumin (43K), carbonic anhydrase (31K), soybean trypsin inhibitor (21K) and lactalbumin (14K).

EXAMPLE 2

Monoclonal antibodies against prosomal proteins

In its general aspect, the method according to the invention for obtaining hybridoma cell lines producing antibodies against proteins of prosomes comprises the following stages:

1) immunization of mice with a given amount of the desired proteins prepared according to Example 1;
2) removal of the spleen of the immunized mice and separation of the spleen cells;
3) fusion of the spleen cells thereby obtained with mouse myeloma cells in the presence of a fusion promoter;
4) culturing of the hybrid cells obtained in a selective medium on which the unfused myeloma cells do not grow, and in the presence of suitable nutrient components;
5) selection of the cells which produce the desired antibody and cloning of these cells.

The first stage of this method, namely the immunization of the mice, is carried out so as to stimulate the memory of the cells for the synthesis of antibody.

The immunization protocol consists in injecting subcutaneously and intraperitoneally, three successive times at intervals of approximately 2 to 3 weeks, a given amount of the prosome protein and, 4 days before the fusion and after a rest period of 2 months, giving a booster intravenously and intraperitoneally with the same amount of prosome protein.

The amount of prosome protein used at each injection is approximately 20 to 50 μg per mouse.

The mice immunized in this manner are then sacrificed and their spleens are removed and treated for recovering the spleen cells, in RPMI 1640 medium as defined, for example, by MOORE et al. "Culture of Normal Human Leucocytes" J.A.M.A. 199, 519–524, 1967.

The fusion of the cells, which constitutes the third stage of the method of the invention, consists in mixing the spleen cells of mice immunized against a prosome protein and mouse myeloma cells, according to the technique of KOHLER and MILSTEIN [Nature 256, 495–497 (1975)] in the presence of the fusion promoter polyethylene glycol. Myeloma cells are used in a ratio of 1:10 with respect to the spleen cells.

After incubation with agitation at 37° C. for one minute in the presence of polyethylene glycol, the cells are washed in RPMI 1640 medium and resuspended in the same medium, and are then cultured on a selective medium which is suitable for the growth of the hybrid cells.

Since the myeloma cells are devoid of the enzyme hypoxanthine:guanine phosphoribosyltransferase, they do not reproduce on media containing hypoxanthine, aminopterin and thymidine. In consequence, the selective medium for the growth of the hybridoma cells contains hypoxanthine, aminopterin and thymidine.

The cells which produce the antibody against the desired prosome protein are then selected and cloned.

The production of substantial amounts of monoclonal antibody can be carried out either by culturing in vitro the hybrid cells selected in this manner, or by injecting them into mice and harvesting, after approximately 15 days, their ascitic fluid which contains the antibody sought.

The monoclonal antibodies thereby obtained are stored by freezing at −20° C.

EXAMPLE 3

Preparation of antibodies against proteins p 27K and p 31K of duck prosomes

The term "protein p 27K" and "protein p 31K" designates in the present example the prosomal protein having a molecular weight of 27 000 and 31 000 respectivelly.

The duck 20S globin mRNPs obtained according to the procedure described by VINCENT et al. [in Eur. J. Biochem. 112, 617–633 (1980)] were dissociated by treatment with 0.5M KCl into four major sub-complexes of sedimentation coefficients 4S, 13S, 16S and 19S (prosome). To obtain antibodies against the specific prosome proteins, Balb/c mice were injected intraperitoneally and subcutaneously with 20 μg of prosome (particle of sedimentation 19S obtained above) in the presence of Freund's adjuvant according to the immunization protocol defined in Example 2 above. One week after the second injection, the mouse serum was sampled and the presence of antibodies detected by ELISA and immunoelectrotransfer techniques.

Two months after the third injection, a booster was performed intravenously and interperitoneally with the same amount of prosome and, four days later, the mice were sacrificed, their spleens removed and the spleen cells ($10^8$) fused with myeloma cells ($10^7$) of PAI mice [supplied by the laboratory of T. STAEHELIN of HOFFMANN-LA-ROCHE, Basle (Switzerland)] according to the method of KOHLER and MILSTEIN, using polyethylene glycol as a fusion promoter.

The cells which were producing antibodies against prosome proteins were then selected on a selective medium and cloned by the limiting dilution method.

The detection of the hybrid cells which were producing antibodies was performed by the ELISA method and the immunoelectrotransfer method.

For these two tests, the 20S globin mRNP particle was used as antigen and the positive clones, that is to say the clones which were producing antibodies against the prosome proteins p 27K and p 31K, were selected with this antigen.

The cell lines producing monoclonal antibodies against the p 27K and p 31K prosomal proteins were deposited at the Collection National de Culture de Microorganisms of the Pasteur Institute under the no.'s I-588 and I-589, respectively.

The cell line producing anti-p 27K antibodies (indicated by the internal notation IB5) produces antibodies of the class IgG1, having an isoelectric pH of about 5.9.

The cell line producing anti-p 31K antibodies (indicated by the internal notation AA4) produces antibodies also of the class IgG1, having an isoelectric pH of about 5.2.

Figures 1, 3A:
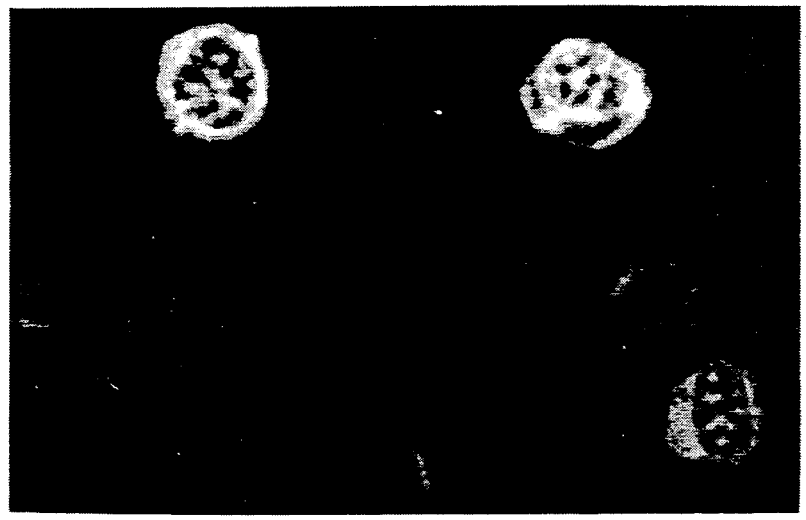

FIG. 1, attached, shows:

the sedimentation profile of the duck 20S globin mRNP particle in a sucrose gradient in the presence of 0.5 m KCl, observed at 254 nm (FIG. 1A), a photograph of the one-dimensional SDS-polyacrylamide gel of the proteins in the fraction of the gradient shown at A, the proteins being stained with Coomassie blue (FIG. 1B). In this figure, M indicates the molecular weight markers and the zone 3–6 corresponds to the duck prosome proteins, a photograph of the proteins in a gel homologous with the gel shown at B after transfer to nitrocellulose paper and successive reaction (ELISA) with the monoclonal antibodies against protein p 27K (FIG. $1C_1$) and protein p 31K (FIG. $1C_2$) according to the same procedure as that described in Example 4 below.

EXAMPLE 4

Demonstration of the universal nature of the 27K and 31K proteins using monoclonal antibodies obtained in Example 3

To show the specificity and universality of the monoclonal antibodies against prosomal proteins the duck, mouse and Hela cell prosome proteins obtained after dissociation on a sucrose gradient in 0.5M potassium chloride were subjected to one-dimensional gel electrophoresis and stained with Coomassie blue. The proteins of homologous gels were transferred from the gel to nitrocellulose paper by immunoelectrotransfer according to the technique of TOWBIN et al. (Proc. Natl. Acad. Sci. USA 76, 4350–4354). After the transfer, the nitrocellulose paper was immersed overnight at 4° C. in PBS phosphate buffer containing 3% of bovine serum albumin to remove the non-specific reaction products. The paper was then incubated overnight at 18° C. with the antibody against prosomal proteins obtained from Example 3 originating from ascitic fluid and diluted in PBS (1:600). The paper was then washed 4 times with PBS and then incubated for three hours with a peroxidase-labelled antibody (goat antibody against mouse IgG) diluted in PBS (1:1000) and containing 10% of goat serum. After the reaction, the paper was washed again with PBS and the enzyme reaction visualized with 4-chloro-1-naphthol for 5 to 10 min.

In this experiment, the antibodies obtained in Example 3 against duck prosome protein p 27K and p 31K reacted positively with the duck, mouse and Hela cell prosome proteins.

Figures 2, 3A:
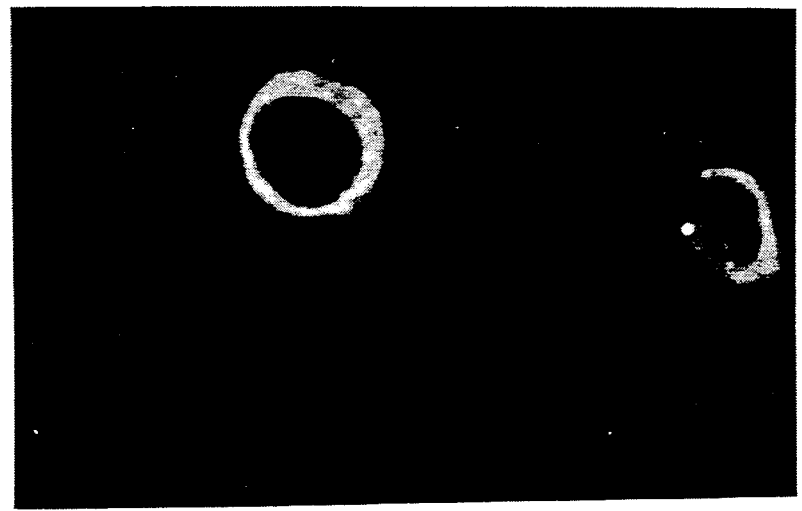

FIG. 2, attached, shows:

at A, a photograph of the gel from electrophoresis of the proteins of duck erythrocytes (a), mouse erythrocytes (b) and Hela cells (c), after staining with Coomassie blue, M denoting the molecular weight markers;

at B, a photograph of the proteins in a homologous gel after transfer to nitrocellulose paper and reaction with the monoclonal antibody against protein p 31K;

at C, a photograph of the proteins after transfer to nitrocellulose paper and reaction with the monoclonal antibody against protein p 27K.

EXAMPLE 5

Use of the monoclonal antibodies against prosomal proteins for the identification of prosomes Cyto-immunofluorescence studies were performed with different types of cells for identification of the prosomal antigens.

In a first stage, a smear was made of cells which were fixed using 3% paraformaldehyde in PBS for 15 minutes at room temperature. After this fixation stage, the cells were rendered permeable with 0.1% "Triton×100" for 5 min. and then preincubated with 1% rabbit serum and 0.1% bovine serum albumin in PBS to suppress non-specific reactions.

After four successive washes with PBS, the cells were incubated for 1 h. in. a moist chamber with the monoclonal antibody against protein p 27K or the monoclonal antibody against protein p 31K. The cells were then washed 3 times for 30 min. and incubated with a second, fluorescein-labelled antibody (rabbit antibody against mouse IgG/FITC) for 30 min. in the dark. The cells were then observed in the light microscope and the cells containing prosomal proteins determined, these cells being the fluorescent cells.

Figures 1, 4A:
Figures 2, 4B:

This experiment was performed with duck peripheral blood cells and Hela cells. FIGS. 3 and 4, attached, are the photographs of the cells observed in the microscope.

In these figures:

photograph $3A_1$ is that of duck peripheral blood cells which have reacted with the antibody against protein p 27K;

photograph $3A_2$ is that of duck peripheral blood cells which have reacted with the antibody against the protein p 31K. In these two photographs, it is observed that the adult cells are virtually devoid of fluorescence whereas the young cells, which are fluorescent to a greater or lesser extent, show the presence of prosomal proteins in an intensity and a distribution which depend on their degree of differentiation and on the type of monoclonal antibody used:

FIG. $4B_1$ shows Hela cells incubated with the monoclonal antibody against protein p 27K;

FIG. $4B_2$ shows Hela cells incubated with the monoclonal antibody against protein p 31K. In this case, all the cells are fluorescent and hence all contain prosomal proteins. It will be noted that the staining differs according to the type of prosomal antibody used.

This experiment shows that the monoclonal antibodies according to the invention can be used for studying the differentiation of living human or animal cells.

We claim:

1. A monoclonal antibody specifically directed against a prosomal protein of a prosome, said prosome having a sedimentation coefficient of approximately 19S.

2. The monoclonal antibody of claim 1, produced by one of the cell lines deposited with the Collection Nationale de Cultures des Microorganismes of the Pasteur Institute at Paris, under accession numbers I-588 and I-589.

3. Immortalized cell line producing a monoclonal antibody according to claim 2, which is a hybridoma cell line or a transformed cell line.

4. The monoclonal antibody of claim 1, wherein said prosomal protein against which the monoclonal antibody is directed has a molecular weight between about 19,000 and about 50,000 daltons.

5. The monoclonal antibody of claim 1, wherein said prosomal protein against which the monoclonal antibody is directed has a molecular weight of about 27,000 daltons.

6. The monoclonal antibody of claim 1, wherein said prosomal protein against which the monoclonal antibody is directed has a molecular weight of about 31,000 daltons.

7. A monoclonal antibody specifically directed against a prosomal protein having a molecular weight of about 27K or 31K daltons by SDS-polyacrylamide gel electrophoresis, said prosomal protein being from a prosome having a sedimentation coefficient of approximately 19S.

8. Immortalized cell line producing a monoclonal antibody according to claim 7, which is a hybridoma cell line or a transformed cell line.

9. A method of detecting a cancer in a living being comprising deriving a sample from said living being, incubating said sample with monoclonal antibodies specifically directed against a prosomal protein, said prosomal protein being from a prosome having a sedimentation coefficient of approximately 19S, wherein the monoclonal antibodies are directly or indirectly provided with a label, and subsequently determining by means of the activity of the label, the binding of said monoclonal antibodies to the prosomal protein whereby the presence of a cancer is determined.

10. Method according to claim 9, wherein the monoclonal antibody is directed against one of the prosomal proteins of p 27K or p 31K molecular weight by SDS-polyacrylamide gel electrophoresis.

11. The method according to claim 9, wherein the sample is incubated with monoclonal antibodies produced by a cell line deposited with the Collection Nationale de Cultures des Microorganismes of the Pasteur Institute at Paris under accession numbers I-588, I-589 or mixtures thereof.

12. The method of claim 9 wherein said cancer is leukemia.

13. A diagnostic reagent, comprising a monoclonal antibody directed against a prosomal protein, said prosomal protein being from a prosome having a sedimentation coefficient of approximately 19S, coupled to a label.

14. Diagnostic reagent according to claim 13, wherein the monoclonal antibody is specifically directed against one of the prosomal proteins of p 27K or p 31K molecular weight by SDS-polyacrylamide gel electrophoresis.

15. The diagnostic reagent of claim 13, wherein the monoclonal antibody is produced by a cell line deposited with the Collection Nationale de Cultures des Microorganismes of the Pasteur Institute at Paris, under accession numbers I-588 or I-589.

16. A monoclonal antibody specifically directed against a prosomal protein, said monoclonal antibody produced by a method comprising:
 a) immunizing an animal with a prosomal protein, said prosomal protein obtained by separating prosomes having a sedimentation coefficient of approximately 19S from other cellular complexes by fractionation, and collecting prosomes therefrom;
 b) removing the spleen from said immunized animal;
 c) separating the spleen cells;
 d) immortalizing said spleen cells;
 e) culturing the cells thus obtained in a medium selective for immortalized cells; and selecting immortalized cells which produce monoclonal antibodies specifically directed against said prosomal protein.

17. A monoclonal antibody specifically directed against a prosomal protein, said monoclonal antibody produced by a method comprising:
 a) immunizing an animal with a prosomal protein, said prosomal protein obtained by:
  i) separating prosomes having a sedimentation coefficient of approximately 19S from other cellular complexes by differential fractionation, and collecting prosomes therefrom, and ii) extracting and separating prosomal proteins from said prosomes by gel electrophoresis;
b) removing the spleen from said immunized animal;
c) separating the spleen cells;
d) fusing said spleen cells with myeloma cells;
e) culturing the hybrid cells thus obtained in a medium selective for fused cells; and selecting fused cells which produce monoclonal antibodies specifically directed against said prosomal protein.

* * * * *